United States Patent [19]

Delpy et al.

[11] Patent Number: 5,523,471
[45] Date of Patent: Jun. 4, 1996

[54] PROCESS FOR THE PREPARATION OF ETHER-SULPHONATES

[75] Inventors: Klaus Delpy, Dietzenbach; Fritz Engelhardt, Frankfurt am Main; Ralf Zerrer, Alzenau; Dirk Bühring, Frankfurt am Main, all of Germany

[73] Assignee: Hoechst Aktiengesellschaft, Germany

[21] Appl. No.: 520,712

[22] Filed: Aug. 29, 1995

[30] Foreign Application Priority Data

Sep. 1, 1994 [DE] Germany ............... 44 31 056.0

[51] Int. Cl.$^6$ .................................... C07C 381/00
[52] U.S. Cl. ................................................ 562/110
[58] Field of Search ................................ 562/110

[56] References Cited

U.S. PATENT DOCUMENTS

| | | | |
|---|---|---|---|
| 2,535,677 | 12/1950 | Hollander et al. | 562/111 |
| 4,091,014 | 5/1978 | Johnson, Jr. et al. | 562/42 |
| 4,226,807 | 10/1980 | McCoy | 562/42 |
| 4,465,602 | 8/1984 | McCoy | 507/255 |

Primary Examiner—José G. Dees
Assistant Examiner—Joseph M. Conrad, III
Attorney, Agent, or Firm—Connolly & Hutz

[57] ABSTRACT

The present invention relates to a process for the preparation of ether-sulphonates of high purity, substantially free from extraneous salts, of the general formula I $$R^1-[O-(CR^2R^{2'}-CR^5R^{5'}SO_3M \qquad I$$

in which
$R^2$ to $R^5$, $R^{2+}$ to $R^{5'}$, M, x and y are defined as given in claim 1 by reacting a compound of the general formula II $$R^1-[O-(CR^2R^{2+}-CR^3R^{3'})_x]_y-OH \qquad II$$

with a compound of the general formula III $$HO-CR^4R^{4'}CR^5R^{5'}-SO_3M \qquad III$$

in the presence of a compound of the general formula IV $$MOH \qquad IV$$

followed by neutralization of the compound of the general formula IV with an acid, characterized in that the acid employed is a compound of the general formula V $$R^1-[O-(CR^2R^{2'}-CR^3R^{3'})_x]_y-OCR^4R^{4'}CR^5R^{5'}SO_3H \qquad V$$

10 Claims, No Drawings

PROCESS FOR THE PREPARATION OF ETHER-SULPHONATES

The present invention relates to a process for the preparation of ether-sulphonates of high purity, substantially free from extraneous salts, by reaction of alcohols with hydroxyalkanesulphonic acid salts under basic catalysis.

Ether-sulphonates are important chemical intermediates and are utilized for a series of industrial reactions.

Accordingly, processes for their preparation have already been disclosed. For example, U.S. Pat. Nos. 2,535,677, 4,091,014, 4,226,807 and 4,465,602 describe the reaction of alcohols with hydroxyalkanesulphonic acid salts under basic catalysis, the basic catalyst having to be neutralized by addition of acid after the end of the reaction. The salt formed during neutralization remains in the end product, so that it is impossible to obtain by these processes products of high purity, especially products free from extraneous salts. No process has hitherto been disclosed which gives ether-sulphonates of high purity, substantially free from extraneous salts, despite the considerable advantages which would attach to such a process.

It has now been found surprisingly that ether-sulphonates of high purity, substantially free from extraneous salts, can be obtained by reaction of alcohols with hydroxyalkanesulphonic acid salts under basic catalysis if, after the end of the reaction, neutralization is carried out with the ether-sulphonic acid conjugated to the ether-sulphonate prepared.

The present invention relates accordingly to a process for the preparation of ether-sulphonates of high purity, substantially free from extraneous salts, of the general formula I

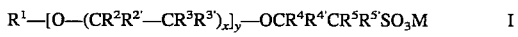
$$R^1-[O-(CR^2R^{2'}-CR^3R^{3'})_x]_y-OCR^4R^{4'}CR^5R^{5'}SO_3M \quad I$$

in which
$R^1$ is hydrogen, $(C_1-C_{22})$-alkyl, $(C_2-C_{22})$-alkenyl, $(C_3-C_8)$-cycloalkyl, alkyl, $(C_6-C_{14})$-aryl or $(C_6-C_{14})$-aryl-$(C_1-C_8)$-alkyl;
$R^2$ to $R^5$ and $R^{2'}$ to $R^{5'}$ are independently of one another hydrogen or $(C_1-C_4)$-alkyl;
M is an alkali metal, the ammonium group or a substituted ammonium group;
x is an integer from 1 to 20; and
y is an integer from 0 to 20,
in which if x>1 the radicals $R^2$ the radicals $R^{2'}$, the radicals $R^{3'}$ and the radicals $R^3$ are in each case also independent of one another, and
in which $R^1$ cannot be hydrogen if y=0, by reacting a compound of the general formula II

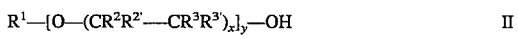
$$R^1-[O-(CR^2R^{2'}-CR^3R^{3'})_x]_y-OH \quad II$$

with a compound of the general formula III

$$HO-CR^4R^{4'}CR^5R^{5'}-SO_3M \quad III$$

in the presence of a compound of the general formula IV

$$MOH \quad IV$$

followed by neutralization of the compound of the general formula IV with an acid, characterized in that the acid employed is a compound of the general formula V

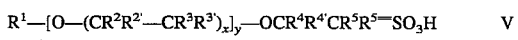
$$R^1-[O-(CR^2R^{2'}-CR^3R^{3'})_x]_y-OCR^4R^{4'}CR^5R^{5'}-SO_3H \quad V$$

Alkyl groups may be straight-chain or branched and are for example methyl, ethyl, n-propyl, isopropyl, n-butyl, isobutyl, sec-butyl, tert-butyl, n-pentyl, 3-methylbutyl, 3-pentyl, n-hexyl, 2-ethylbutyl or 2-ethylhexyl.

Alkyl as $R^1$ preferably has 1 to 5 carbon atoms, particularly preferably 1 to 3 carbon atoms. Alkyl as $R^2$ to $R^1$ and/or $R^{2'}$ to $R^{5'}$ preferably has 1 to 3 carbon atoms.

Cycloalkyl is in particular cyclopropyl, cyclobutyl, cyclopentyl, cyclohexyl, cycloheptyl and cyclooctyl, cyclopentyl and cyclohexyl being preferred. However, cycloalkyl also refers, for example, to dimethylcycloalkyl.

Alkenyl groups may also be straight-chain or branched and correspond, for example, to the abovementioned alkyl groups. Preferred alkenyl groups have 2 to 5 carbon atoms, with vinyl and allyl being particularly preferred.

Aryl groups are preferably phenyl, naphthyl biphenyl or fluorenyl, with phenyl being particularly preferred.

Preferred arylalkyl groups are benzyl and phenethyl.

An alkali metal M is preferably sodium or potassium.

A substituted ammonium group M may be any conventional mono-, di-, tri- or tetra-substituted ammonium group.

An ammonium group M preferably has the formula $NR^6R^7R^8R^9$, where $R^6$, $R^7$, $R^8$ and $R^9$ independently of one another are hydrogen, $(C_1-C_6)$-alkyl, phenyl, substituted phenyl or halogen. Tetra$(C_1-C_4)$-alkylammonium is particularly preferred.

In compounds of the general formula I to be prepared preferably in accordance with the process of the invention
$R^1$ is hydrogen or $(C_1-C_6)$-alkyl
$R^2$ to $R^5$ and $R^{2'}$ to $R^{5'}$ independently of one another are hydrogen or $(C_1-C_3)$-alkyl
M is sodium or potassium
x is an integer from 1 to 4 and
y is an integer from 1 to 10.

In compounds of the general formula I to be prepared particularly preferably in accordance with the process of the invention
$R^1$ is hydrogen
$R^2$, $R^{2'}$, $R^3$ and $R^{3'}$ independently of one another are hydrogen or methyl,
$R^4$, $R^{4'}$, $R^5$ and $R^{5'}$ are hydrogen,
M is sodium or potassium and
x and y are the number 1.

The process according to the invention is a base-catalyzed condensation reaction which is carried out under atmospheric pressure in particular at temperatures of from 150° to 250° C., particularly preferably at 180° C. It is preferred to remove the water formed during the reaction from the reaction mixture by continuous distillation. The reaction times are in general from 2 to 10 hours.

In a preferred embodiment of the preparation process of the invention the compound of the general formula II is employed in a quantity of from 200 to 700 mol %, the compound of the general formula III in a quantity of 100 mol % and the compound of the general formula IV in a quantity of from 10 to 20 mol %.

In a further preferred embodiment, after neutralization of the reaction mixture with a compound of the general formula V, the compound of the general formula III, which is employed in excess, is separated off using a thin-film evaporator. In the course of this procedure it is preferred to maintain a pressure of from 10 to 500 mbar and a temperature of from 120° to 250° C.

The compounds of the general formula II and III are known, can be obtained commercially and/or are accessible by preparation processes known to the person skilled in the art.

The compounds of the general formula V can be obtained simply, by adding an acid of suitable $pK_a$, to a compound of the general formula I obtained from a preceding reaction batch, in a manner known to the person skilled in the art, and isolating the product. Acids which are generally suitable are sulphuric acid, hydrochloric acid or methanesulphonic acid.

If there is not yet any compound of the general formula I present, then compounds of the general formula V prepared by other methods may also be employed.

The compounds of the general formula I prepared by the process according to the invention are of high purity and are substantially free from extraneous salts. In the context of this invention, the term "substantially free from extraneous salts" means that the extraneous-salt content of the compounds of the general formula I prepared according to the invention is not more than 2% by weight.

EXAMPLE 1

Reaction and neutralization 310.1 g (5.0 mol) of 1,2-ethanediol, 148.1 g (1.0 mol) of the sodium salt of 2-hydroxyethane-sulphonic acid (Na isethionate) and 4.0 g (0.1 mol) of sodium hydroxide are placed in a 1 l three-neck flask fitted with KPG stirrer, a heatable 40 cm column with Liebig condenser attached and an internal thermometer.

The reaction mixture is heated with continuous stirring to an internal temperature of 190°–195° C. The jacket temperature of the distillation column is maintained at 110°–195° C. Over the course of 3 h about 18.0 g of water are distilled off from the reaction mixture. After cooling to RT the alkaline product solution is neutralized by adding about 17.0 g (0.1 mol) of 2-(2hydroxyethoxy)ethanesulphonic acid, while stirring continuously.

Work-up

The ether-sulphonate is isolated from the glycol-containing product solution by an operation of thin-film evaporation. In this operation the jacket heating of the evaporator tube is maintained at about 200° C. The vacuum was set at 10 mbar. The sodium salt of 2-(2-hydroxyethoxy)ethanesulphonic acid (Na diglycolsulphonate) is obtained as a colourless distillation residue having a melting range of 140°–150° C. The glycol content is below 1% by weight. The purity is 98.2% by weight and the content of extraneous salts is 0.3% by weight.

If the above procedure is followed but the alkaline product solution obtained is neutralized as is conventional in the prior art, using 9.6 g (0.1 mol) of methanesulphonic acid, then the purity of the ether-sulphonate is 92 to 94% by weight and the content of extraneous salts is from 6 to 8% by weight.

EXAMPLE 2

229.0 g (3.0 mol) of 1,2-propanediol, 148.1 g (1.0 mol) of the sodium salt of 2-hydroxyethane-sulphonic acid and 4.0 g (0.1 mol) of sodium hydroxide are reacted analogously to Example 1.

After the end of the reaction, neutralization is carried out with the sulphonic acid conjugated to the product, and a corresponding work-up is carried out using a thin-film evaporator. The degree of purity is 98.5% by weight and the content of extraneous salts is 0.8% by weight.

If the above procedure is followed but the alkaline product solution obtained is neutralized as is conventional in the prior art, using methanesulphonic acid, the purity of the ester-sulphonate is 93.5% by weight and the content of extraneous salt is 5.4% by weight.

EXAMPLE 3

390.3 g (3.0 mol) of 2-ethylhexanol, 148.1 g (1.0 mol) of the sodium salt of 2-hydroxyethane-sulphonic acid and 8.0 g (0.2 mol) of sodium hydroxide are reacted analogously to Example 1.

The reaction temperature is 210°–220° C. and the reaction time is 6 h. The jacket temperature of the heated column is set at 160°–180° C. After the end of the reaction, neutralization is carried out with the sulphonic acid conjugated to the product, and working up is carried out using a thin-film evaporator as described in Example 1.

The degree of purity is 98% by weight and the content of extraneous salts is 1.3% by weight.

If the above procedure is followed but the alkaline product solution obtained is neutralized as is conventional in the prior art, using methanesulphonic acid, the purity of the ether-sulphonate is 90.6% by weight and the content of extraneous salts is 8.5% by weight.

EXAMPLE 4

296.2 g (4.0 mol) of n-butanol 148.1 g (1.0 mol) of the sodium salt of 2-hydroxyethane-sulphonic acid and 4.0 g (0.2 mol) of sodium hydroxide are reacted analogously to Example 1.

The reaction temperature is 205°–210° C. and the reaction time is 8 h.

The jacket temperature of the column is set at 105°–110° C.

After neutralization with the sulphonic acid conjugated to the product and working up by means of a thin-film evaporator, the product is obtained in a purity of 98.5% by weight with a content of extraneous salts of 0.6% by weight.

Neutralization with methanesulphonic acid according to the prior art gives a purity of 88.5% by weight and a content of extraneous salts of 10.5% by weight.

EXAMPLE 5

530.2 g (5.0 mol) of n-butanol 148.1 g (1.0 mol) of the sodium salt of 2-hydroxyethane-sulphonic acid and 8.0 g (0.2 mol) of sodium hydroxide are reacted analogously to Example 1.

The reaction temperature is 200°–210° C. and the reaction time is 6 h.

The jacket temperature of the column is set at 160°–180° C.

After neutralization with the sulphonic acid conjugated to the product followed by working up using a thin-film evaporator, the product is obtained in a purity of 98.1% by weight, and the content of extraneous salts is 0.2% by weight.

Neutralization with methanesulphonic acid according to the prior art gives a purity of 90% by weight and a content of extraneous salts of 8% by weight.

We claim:

1. Process for the preparation of ether-sulphonates of high purity, substantially free from extraneous salts, of the formula I $$R^1-[O-(CR^2R^{2'}-CR^3R^{3'})_x]_y-OCR^4R^{4'}CR^5R^{5'}SO_3M \quad \text{I}$$

in which
- $R^1$ is hydrogen, $(C_1-C_{22})$-alkyl, $(C_2-C_{22})$-alkenyl, $(C_3-C_8)$-cycloalkyl, $(C_6-C_{14})$-aryl or $(C_6-C_{14})$-aryl-$(C_1-C_8)$-alkyl;
- $R^2$ to $R^5$ and $R^{2'}$ to $R^{5'}$ are independently of one another hydrogen or $(C_1-C_4)$-alkyl;
- M is an alkali metal, the ammonium group or a substituted ammonium group;
- x is an integer from 1 to 20; and
- y is an integer from 0 to 20, in which if x>1, then there are more than one of each of the radicals $R^2$, $R^{2'}$, $R^3$ and $R^{3'}$, then the radicals $R^2$, the radicals $R^{2'}$, the radicals $R^3$ and the radicals $R^{3'}$ are in each case also independent of one another and, in which $R^1$ cannot be hydrogen if y=0,
comprising reacting a compound of the formula II $$R^1-[O-(CR^2R^{2'}-CR^3R^{3'})_x]_y-OH \quad \text{II}$$

with a compound of the formula III $$HO-CR^4R^{4'}CR^5R^{5'}-SO_3M \quad \text{III}$$

in the presence of a compound of the formula IV $$MOH \quad \text{IV}$$

followed by neutralizing the compound of the formula IV with an acid of the formula V $$R^1-[O-(CR^2R^{2'}-CR^3R^{3'})_x]_y-OCR^4R^{4'}CR^5R^{5'}SO_3H \quad \text{V}$$

2. The process according to claim 1, wherein
- $R^1$ is hydrogen or $(C_1-C_6)$-alkyl
- $R^2$ to $R^5$ and $R^{2'}$ to $R^{5'}$ independently of one another are hydrogen or $(C_1-C_3)$-alkyl
- M is sodium or potassium
- x is an integer from 1 to 4 and
- y is an integer from 1 to 10.

3. The process according to claim 2, wherein $R^1$ is $(C_1-C_3)$-alkyl.

4. The process according to claim 1, wherein
- $R^1$ is hydrogen
- $R^2$, $R^{2'}$, $R^3$ and $R^{3'}$ independent of one another are hydrogen or methyl,
- M is sodium or potassium and
- x and y are the number 1.

5. The process according to claim 4, wherein the compound of the formula II is employed in a quantity of from about 200 to about 700 mol %, the compound of the formula III in a quantity of about 100 mol % and the compound of the formula IV in a quantity of from about 10 to about 20 mol %.

6. The process according to claim 5, wherein after neutralization of the reaction mixture with a compound of the formula V, the compound of the formula II, which is employed in excess, is separated off using a thin-film evaporator.

7. The process according to claim 6, wherein the reaction is carried out at a temperature range from about 150° to about 250° C.

8. The process according to claim 1, wherein the compound of the formula II is employed in a quantity of from about 200 to about 700 mol %, the compound of the formula III in a quantity of about 100 mol % and the compound of the formula IV in a quantity of from about 10 to about 20 mol %.

9. The process according to claim 1, wherein after neutralization of the reaction mixture with a compound of the formula V, the compound of the formula II, which is employed in excess, is separated off using a thin-film evaporator.

10. The process according to claim 1, wherein the reaction is carried out at a temperature range from about 120° to about 250° C.

* * * * *